701/96

United States Patent
Kolisetty et al.

(10) Patent No.: US 10,343,682 B2
(45) Date of Patent: Jul. 9, 2019

(54) VEHICLE OPERATION BASED ON ACTIVITY TRACKING

(71) Applicant: Ford Global Technologies, LLC, Dearborn, MI (US)

(72) Inventors: Aiswarya Kolisetty, Troy, MI (US); Johannes Geir Kristinsson, Ann Arbor, MI (US); Joseph Wisniewski, Royal Oak, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 630 days.

(21) Appl. No.: 14/517,256

(22) Filed: Oct. 17, 2014

(65) Prior Publication Data

US 2016/0107646 A1   Apr. 21, 2016

(51) Int. Cl.
*A61B 5/00* (2006.01)
*A61B 5/0205* (2006.01)
(Continued)

(52) U.S. Cl.
CPC ........... *B60W 30/16* (2013.01); *A61B 5/0022* (2013.01); *A61B 5/0205* (2013.01); *A61B 5/02055* (2013.01); *A61B 5/02438* (2013.01); *A61B 5/1112* (2013.01); *A61B 5/1118* (2013.01); *A61B 5/18* (2013.01); *A61B 5/222* (2013.01); *A61B 5/4809* (2013.01); *A61B 5/681* (2013.01);
(Continued)

(58) Field of Classification Search
CPC . A62B 2562/0219; A62B 5/1118; A62B 5/18; A62B 5/681; A62B 5/7275; B60W 30/12; B60W 2040/0827; G60K 9/00845; G60K 9/00798; G60K 2009/00939

USPC ........................................................ 701/96
See application file for complete search history.

(56) References Cited

U.S. PATENT DOCUMENTS 8,109,858 B2   2/2012  Redmann
8,615,377 B1  12/2013  Yuen et al.
(Continued)

FOREIGN PATENT DOCUMENTS

WO        2013121302 A2    8/2013

OTHER PUBLICATIONS https://checkout.lark.com/ProductDetails.asp?ProductCode= larklife, LarkLife, 24-Hour Exercise, Diet and Sleep Coaching System, printed on Jul. 8, 2014, pp. 1-2.
(Continued)

*Primary Examiner* — Charles J Han
(74) *Attorney, Agent, or Firm* — Frank Lollo; Brooks Kushman P.C.

(57) ABSTRACT

A vehicle includes a vehicle computing system (VCS) and an adaptive cruise control module, a lane departure warning (LDW) module, a navigation system, or an alert mechanism (e.g., audible, visual or tactile). The VCS communicates with an activity tracking device worn by a vehicle driver. The activity tracking device detects and records biometric characteristics of the driver, and is capable of exchanging data with the VCS. The VCS generates at least one output signal based on data from the activity tracking device. An adaptive cruise control module may increase the distance between the vehicle and a tracking vehicle based on the signal. A navigation system may generate a recommended parking location based on a difference between step goals and current steps detected by the activity tracking device.

6 Claims, 6 Drawing Sheets

(51) Int. Cl.
| | |
|---|---|
| A61B 5/11 | (2006.01) |
| A61B 5/22 | (2006.01) |
| G16H 40/67 | (2018.01) |
| B60W 50/14 | (2012.01) |
| B60W 50/16 | (2012.01) |
| A61B 5/024 | (2006.01) |
| A61B 5/021 | (2006.01) |
| B60W 30/16 | (2012.01) |
| B60W 30/12 | (2006.01) |
| A61B 5/18 | (2006.01) |
| G01C 21/34 | (2006.01) |
| G06F 19/00 | (2018.01) |
| G01C 21/36 | (2006.01) |

(52) U.S. Cl.
CPC ............ *A61B 5/743* (2013.01); *A61B 5/746* (2013.01); *B60W 30/12* (2013.01); *B60W 50/14* (2013.01); *B60W 50/16* (2013.01); *G01C 21/3423* (2013.01); *G06F 19/00* (2013.01); *G16H 40/67* (2018.01); *A61B 5/021* (2013.01); *A61B 5/024* (2013.01); *A61B 5/4815* (2013.01); *A61B 5/6838* (2013.01); *A61B 5/7455* (2013.01); *A61B 2560/0214* (2013.01); *A61B 2560/0242* (2013.01); *A61B 2562/0219* (2013.01); *B60W 2050/143* (2013.01); *B60W 2540/22* (2013.01); *B60W 2550/30* (2013.01); *G01C 21/3629* (2013.01); *G01C 21/3641* (2013.01); *G01C 21/3685* (2013.01)

(56) References Cited

U.S. PATENT DOCUMENTS

| | | | |
|---|---|---|---|
| 8,712,724 | B2 | 4/2014 | Yuen et al. |
| 9,855,945 | B2 | 1/2018 | Fung et al. |
| 2010/0039249 | A1* | 2/2010 | Schmitz ............... B60K 28/066 340/439 |
| 2010/0167876 | A1 | 7/2010 | Cheng |
| 2010/0331147 | A1 | 12/2010 | Mikan et al. |
| 2011/0003664 | A1 | 1/2011 | Richard |
| 2014/0081179 | A1* | 3/2014 | Moore-Ede ........... A61B 5/1118 600/595 |
| 2014/0143038 | A1 | 5/2014 | Tropper et al. |
| 2014/0275854 | A1* | 9/2014 | Venkatraman ......... A61B 5/721 600/301 |

OTHER PUBLICATIONS

Vollmer, Patricia, http://archive.wired.com/geekmom/2013/03/mapmyrun-mvp/, MapMyRun MVP: A Revolution in Workout Statistics, Mar. 27, 2013, pp. 1-7.

* cited by examiner

VEHICLE OPERATION BASED ON ACTIVITY TRACKING

TECHNICAL FIELD

This application is generally related to the operation of vehicle systems based on driver activity tracking with respect to biometric characteristics.

BACKGROUND

Improvements in three-dimensional accelerometers have been instrumental in increasing the acceptance of personal activity tracking devices (ATs). ATs can measure movement of the wearer and are able to detect and record physical activity such as walking, running and exercising. Some ATs have the capability of detecting other biometric characteristics such as heart rate. ATs also may be equipped with connection means including but not limited to Bluetooth, Ethernet, USB, WiFi, and IrDA and are used to connect with a mobile phone running application software or to a server connected with the cloud. Use of the ATs allows a user to enter fitness goals such as goal of how many steps to walk over a predetermined time (e.g., day, week, month), how many hours to sleep over a predetermined time (e.g., 24 hours, 48 hours, week), and quality of sleep based on combination of sleep time and movement detected while sleeping (periods of restlessness).

SUMMARY

A vehicle includes an adaptive cruise control module configured to maintain a distance between the vehicle and a tracking vehicle, and at least one processor. The at least one processor is configured to communicate with a personal activity tracking device capable of detecting at least one biometric characteristic of a driver of the vehicle and control the adaptive cruise control module to increase the distance based on the at least one biometric characteristic.

A vehicle includes a lane detection module configured to generate an alert based on a distance between the vehicle and a lane boundary the vehicle is traveling in, and at least one processor. The at least one processor is configured to communicate with a personal activity tracking device capable of detecting at least one biometric characteristic of a driver of the vehicle and control the lane detection module to increase the distance based on the at least one biometric characteristic.

A vehicle navigation system includes at least one processor configured to communicate with an activity tracking device and output a recommended parking location based on a number of expected steps between the recommended parking location and a destination, and a difference between a desired number of steps and a current number of steps received from the activity tracking device.

A vehicle computing system includes at least one processor configured to communicate with an activity tracking device, and generate an audio message indicative of a recommended route in response to data from the activity tracking device representative of a current heart rate of a driver of the vehicle.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

The embodiments of the present disclosure generally provide for a plurality of circuits or other electrical devices. All references to the circuits and other electrical devices and the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof) and software which co-act with one another to perform operation(s) disclosed herein. In addition, any one or more of the electric devices may be configured to execute a computer-program that is embodied in a non-transitory computer readable medium that is programmed to perform any number of the functions as disclosed.

This disclosure, among other things, proposes systems and methods for a vehicle to interact with an activity tracking device. For example, the activity tracking device worn by a user may have the capability to determine the number of hours the user slept over a period time (e.g., in the last 24, 48 or 96 hours). Also, the activity tracking device may have the ability to monitor the user's heart rate and determine a baseline heart rate corresponding to different activities (e.g., working, sleeping, exercising and walking). When the user enters the vehicle equipped with the system able to interact with an activity tracking device, the vehicle may communicate with the activity tracking device and, based on the user's past sleep and current heart rate or difference between current heart rate and baseline heart rate, activate an alert mechanism.

Another example of the vehicle interaction with an activity tracking device is recommending a parking location. For example, the activity tracking device worn by a user may have the capability to determine a number of steps the user has taken over a period time (e.g., today, in the last 24 hours or in the last week). Based on the number of steps the user has taken over the period time and a target number of steps the user desires to take over the period of time, the vehicle will recommend a parking location, farther from a destination location (e.g., home, office or store) such that a calculated number of additional steps from the parking location to the destination location plus the current number of steps taken by the user is equal or greater than the target number of steps.

Figure 1:
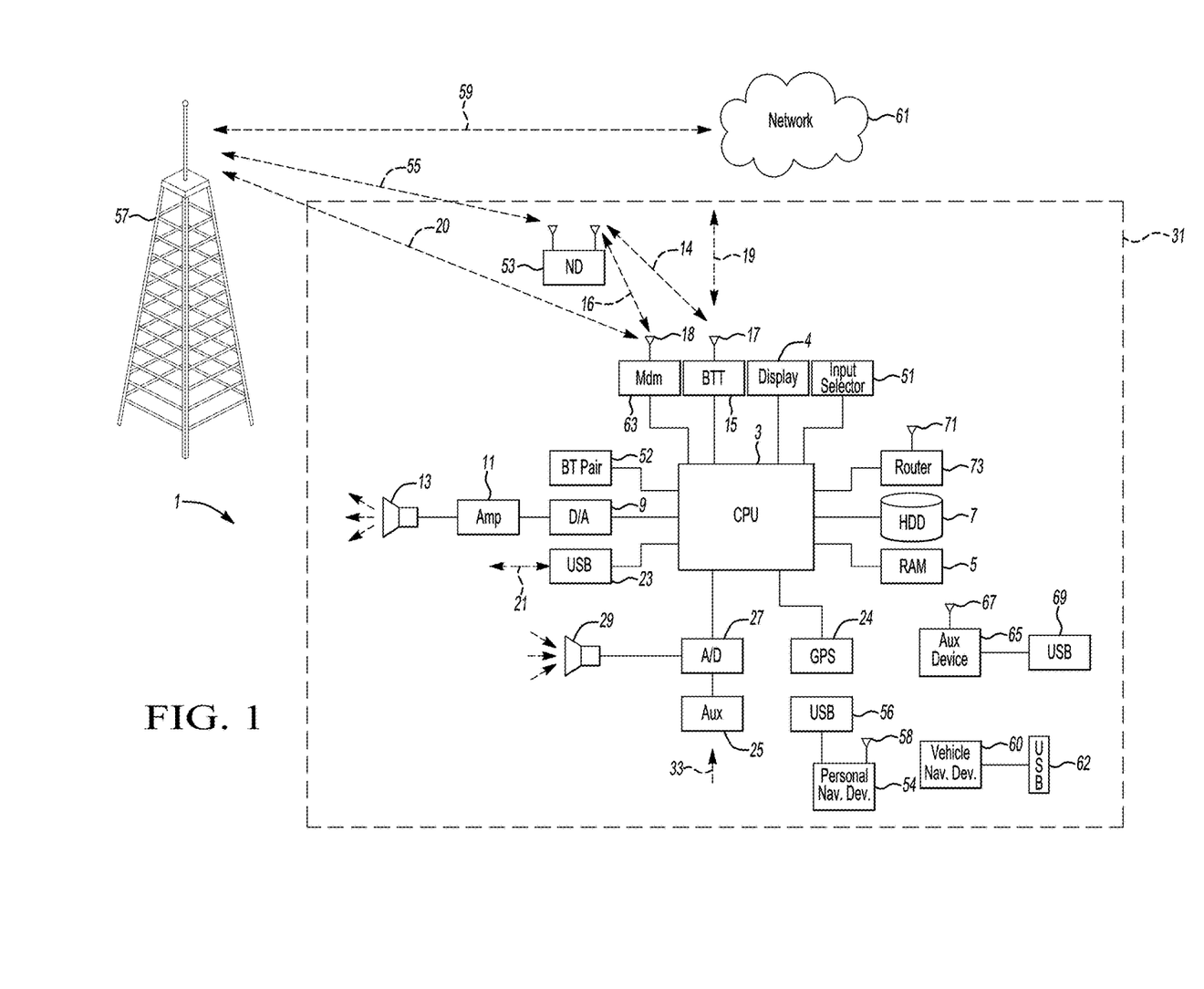
FIG. 1 is an exemplary block topology of a vehicle infotainment system implementing a user-interactive vehicle information display system.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, spoken dialog system with automatic speech recognition and speech synthesis.

In the illustrative embodiment 1 shown in FIG. 1, at least one processor 3 controls at least some portion of the operation of the vehicle-based computing system 1. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory. Non-transitory memory may include both persistent memory and RAM. In general, persistent (non-transitory) memory can include all forms of memory that maintain data when a computer or other device is powered down. These include, but are not limited to, HDDs, CDs, DVDs, magnetic tapes, solid state drives, portable USB drives and any other suitable form of persistent memory.

The processor is also provided with a number of different inputs allowing the user to interface with the processor. In this illustrative embodiment, a microphone 29, an auxiliary input 25 (for input 33), a USB input 23, a GPS input 24, a screen 4, which may be a touchscreen display, and a BLUETOOTH input 15 are all provided. An input selector 51 is also provided, to allow a user to swap between various inputs. Input from both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus, a LIN bus, a MOST bus, an Ethernet bus, or a FlexRay bus) to pass data to and from the VCS (or components thereof).

Outputs from the processor 3 may include, but are not limited to, a visual display 4 and a speaker 13 or stereo system output. The speaker is connected to an amplifier 11 and receives its signal from the processor 3 through a digital-to-analog converter 9. Outputs can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., activity tracking device, cell phone, mobile phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device). Bluetooth is a subset of the IEEE 802 PAN (personal area network) protocols. IEEE 802 LAN (local area network) protocols include WiFi and have considerable cross-functionality with IEEE 802 PAN. Both are suitable for wireless communication within a vehicle. Other wireless communication means that can be used include free-space optical communication (such as IrDA) and non-standardized consumer IR protocols or inductive coupled means including but not limited to near-field communications systems (NFC) such as RFID.

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example). While frequency division multiplexing may be common for analog cellular communication between the vehicle and the internet, and is still used, it has been largely replaced by hybrids of Code Division Multiple Access (CDMA), Time Division Multiple Access (TDMA), Space-Division Multiple Access (SDMA) for digital cellular communication, including but not limited to Orthogonal Frequency-Division Multiple Access (OFDMA), which may include time-domain statistical multiplexing. These are all ITU IMT-2000 (3G) compliant standards and offer data rates up to 2 Mbps for stationary or walking users and 385 Kbps for users in a moving vehicle. 3G standards are now being replaced by IMT-Advanced (4G) which offers 100 Mbps for users in a vehicle and 1 Gbps for stationary users. If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard transceiver (BLUETOOTH, WiFi, NFC) and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58, a vehicle navigation device 60 having a USB 62 or other connection, an onboard GPS device 24, or remote navigation system (not shown) having connectivity to network 61. USB is one of a class of serial networking protocols. IEEE 1394 (FireWire™ (Apple), i.LINK™ (Sony), and Lynx™ (Texas Instruments)), EIA (Electronics Industry Association) serial protocols, IEEE 1284 (Centronics Port), S/PDIF (Sony/Philips Digital Interconnect Format) and USB-IF (USB Implementers Forum) form the backbone of the device-device serial standards. Most of the protocols can be implemented for either electrical or optical communication.

Further, the CPU could be in communication with a variety of other auxiliary devices 65. These devices can be connected through a wireless 67 or wired 69 connection. Auxiliary device 65 may include, but is not limited to, personal media players, wireless health devices, portable computers, and the like.

Also, or alternatively, the CPU could be connected to a vehicle based wireless router 73, using for example a WiFi (IEEE 803.11) 71 transceiver. This could allow the CPU to connect to remote networks in range of the local router 73.

In addition to having exemplary processes executed by a vehicle computing system located in a vehicle, in certain embodiments, the exemplary processes may be executed by a computing system in communication with a vehicle computing system. Such a system may include, but is not limited to, a wireless device (e.g., and without limitation, a mobile phone) or a remote computing system (e.g., and without limitation, a server) connected through the wireless device. Collectively, such systems may be referred to as vehicle associated computing systems (VACS). In certain embodiments particular components of the VACS may perform particular portions of a process depending on the particular implementation of the system. By way of example and not limitation, if a process has a step of sending or receiving information with a paired wireless device, then it is likely that the wireless device is not performing the process, since the wireless device would not "send and receive" information with itself. One of ordinary skill in the art will understand when it is inappropriate to apply a particular VACS to a given solution. In all solutions, it is contemplated that at least the vehicle computing system 1 located within the vehicle itself is capable of performing the exemplary processes.

Figure 2A:
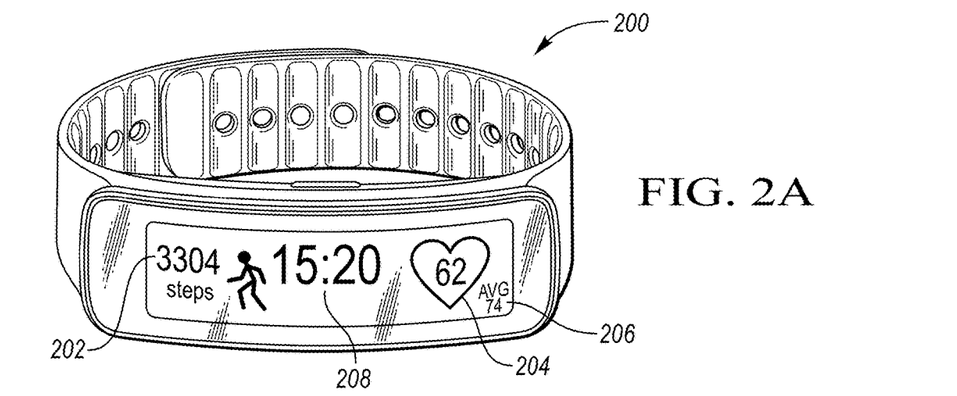
FIG. 2A is an exemplary activity tracking device.

FIG. 2A is an exemplary activity tracking device 200. The activity tracking device 200 is capable of interfacing with the vehicle based computing system 1 via wireless or a wire connection. An activity tracking devices 200 may be a wearable device or may be integrated into a mobile phone. Activity tracking devices 200 may be worn on a user's wrist or may be other small electronic devices available in many forms including clips, necklaces, glasses, lens and medallions (placed in a pocket or subcutaneous). Wireless connections may include Bluetooth, Wifi, Cellular, RFID along with other wireless connection means described above. Wired connections may include serial interfaces or parallel interfaces or a combination of both, including USB or other wired connection means described above. The activity tracking device 200 may include a display capable of indicating biometric characteristics such as number of steps taken over a period of time 202, current heart rate 204 and average heart rate 206. The activity tracking device 200 may also include non-biometric data such as current time 208, altitude, date, calendar information or alerts. The activity tracking device 200 may include sensors to detect a biometric characteristic including movement, heart rate, skin temperature, $O_2$ saturation, skin conductivity, sweat or moisture. Based on the biometric characteristics, the activity tracking device alone or in conjunction with anther processor may determine user aspects such as hours of sleep a user has had within a predetermined period and a sleep quality index of the sleep over a period of time.

The activity tracking device may include one or more inputs such as switches. The input may be a characteristic goal over a period of time. For example, a user may enter a goal of obtaining 5000 steps per day. The activity tracking device 200 may have the ability to detect biometric characteristics and may be able to record the detected biometric characteristics associated with a time of detection. The activity tracking device 200 alone or in conjunction with the VCS may be able to predict the onset of physical conditions based on changes in biometric characteristics. For example, the onset of sleep may be detected by a drop in the user's heart rate below a threshold based on the user's average heart rate. Also, if the driver's heart rate is behaving in an irregular manner from their average or resting heart rate, the VCS may warn the driver of their irregular heart rate and advise that they pull over. Another example may be the detection of the onset of hypoglycemia based on a change in interpretation of sweat, skin conductivity and heart rate or sampling the tears in a person's eyes to determine glucose level. These exemplary predictions may be performed in the activity tracking device 200, the VCS in communication with the activity tracking device 200, or in a mobile phone in communication with both the activity tracking device 200 and VCS. Based on one or more biometric characteristic, VCS may provide a warning, or a recommendation to pull over or travel to the nearest hospital.

Figure 2B:
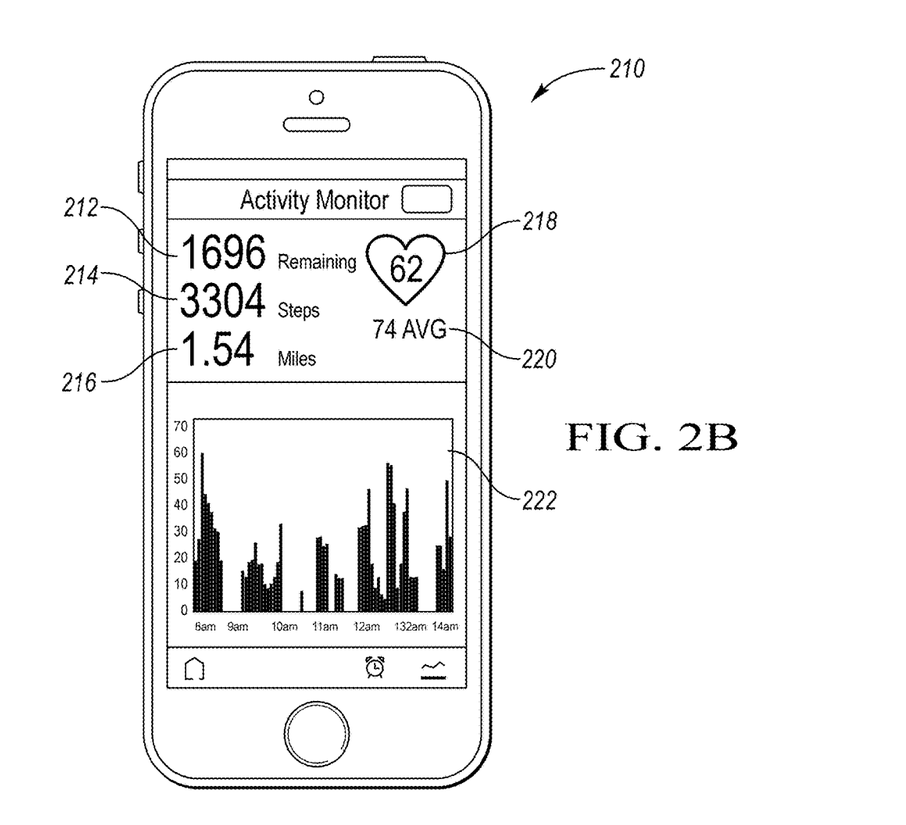
FIG. 2B is an exemplary mobile phone executing a software application based on data received from an activity tracking device.

FIG. 2B is an exemplary mobile phone 210 capable of interfacing with an activity tracking device 200 and a vehicle based computing system (VCS). The mobile phone 210 may communicate with the activity tracking device 200 wirelessly or via a wire connection. The mobile phone 210 may be capable of directly interfacing with the activity tracking device 200 or may require application software to interface with the activity tracking device 200. The mobile phone 210 may include a display capable of displaying one or more biometric characteristics including a statistical representation of the biometric characteristics. For example, the display may indicate that a user has a number of steps remaining 212 to meet a step goal based on a recorded number of steps taken 214 over a predetermined time period. The steps taken 214 may be expressed as a distance 216 (e.g., miles). Also, other biometric characteristics may be displayed such as user heart rate 218 or average heart rate 220. The biometric characteristic may be displayed numerically or graphically. For example, a chart of the number of steps in relationship to time 222 may be shown.

Figure 3A:
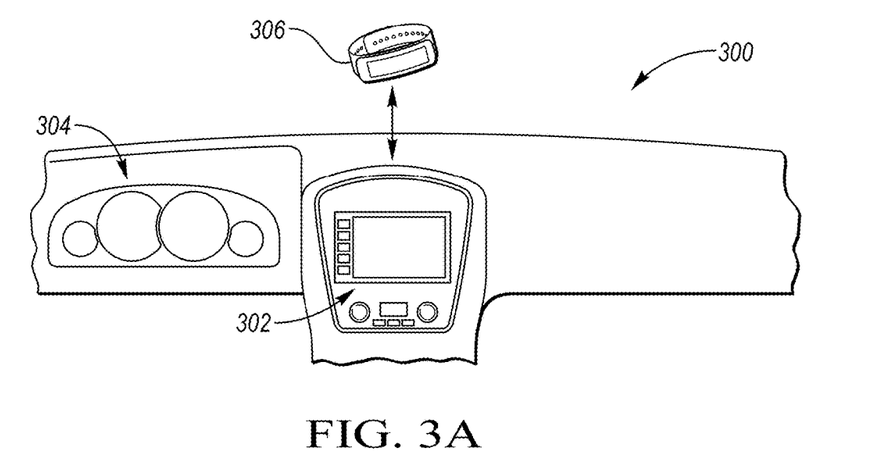
FIG. 3A is an exemplary activity tracking device in communication with a vehicle based computing system.

FIG. 3A is an exemplary illustration of a vehicle interior, specifically a vehicle dash board 300 including a vehicle infotainment system 302 and a vehicle instrument cluster 304. The vehicle infotainment system 302 and vehicle instrument cluster 304 may be coupled via a wire connection including a CAN bus, a Flexray bus, an Ethernet bus, or a MOST bus or may be connected via a wireless connection. The vehicle infotainment system 302 and vehicle instrument cluster 304 may be coupled to other vehicle modules (not shown) including Body Control Modules (BCM), Powertrain Control Modules (PCM), Automatic Braking System (ABS), Electronic Stability Control (ESC), Adaptive Cruise Control Module (ACCM), or Land Departure Warning (LDW) via a wire connection including a CAN bus, a Flexray bus, an Ethernet bus, or a MOST bus. An activity tracking devices 306 may be a wearable device or may be integrated into a mobile phone. An activity tracking device 306 may communicate with the VCS via a wireless or wire connection.

Figure 3B:
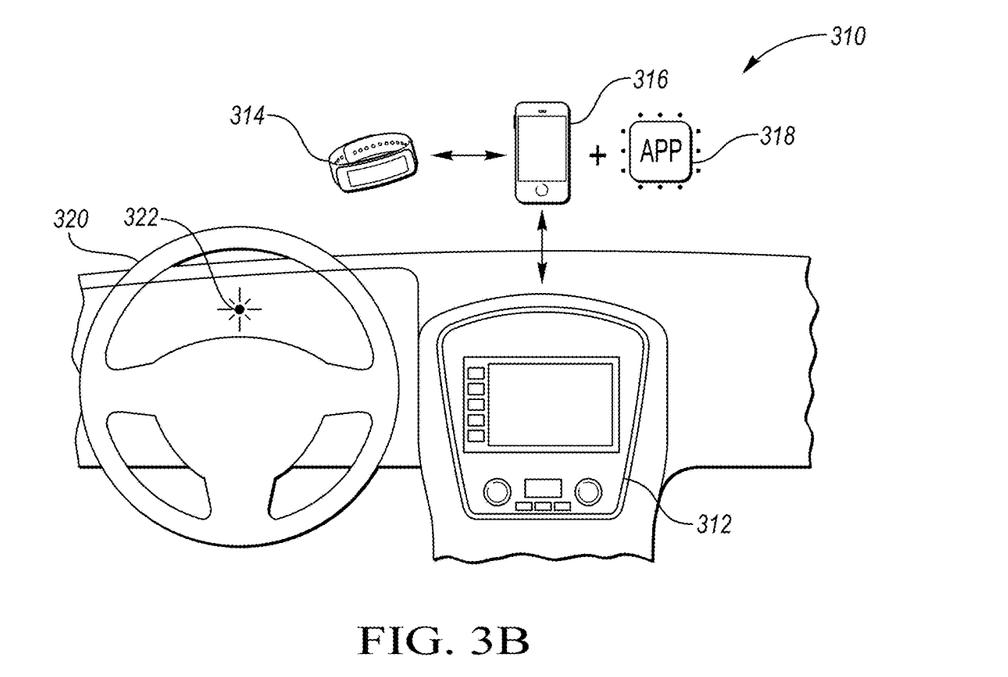
FIG. 3B is an exemplary activity tracking device in communication with a vehicle based computing system via a mobile phone executing a software application.

FIG. 3B is an exemplary illustration of a vehicle interior, specifically the vehicle dash board 310 including a vehicle infotainment system 312. Here, an activity tracking device 314 may communicate with a vehicle computing system 312 via a mobile phone 316 in which the mobile phone 316 may be configured via application software 318 to communicate, wirelessly or via a wire, with vehicle modules including the vehicle computing system 312. Based on the data received from the activity tracking device 314, the vehicle may provide an alert to the driver. The alert may include a vibration mechanism (e.g., vibrating steering wheel mechanism 320, vibrating seat mechanism and vibrating foot pedal mechanism) an illuminating icon 322 within the drivers view or an audible alert (e.g., beep and increase in infotainment module). Also based on the biometric characteristic data from the activity tracking device 314, the vehicle through the adaptive cruise control module may increase the distance between the vehicle and a tracking vehicle, wherein the tracking vehicle is a vehicle directly in front of the vehicle. Another vehicle operation change based on the biometric characteristic data from the activity tracking device 314 may be an increase in sensitivity of a lane departure warning (LDW) module. The change may include an alert, including those listed above, being generated based on a distance the vehicle is from a lane boundary. For example if drowsy driving is detected based on biometric characteristics such as a low heart rate, the LDW may increase in sensitivity by increasing the alert distance from a lane boundary.

Figure 4:
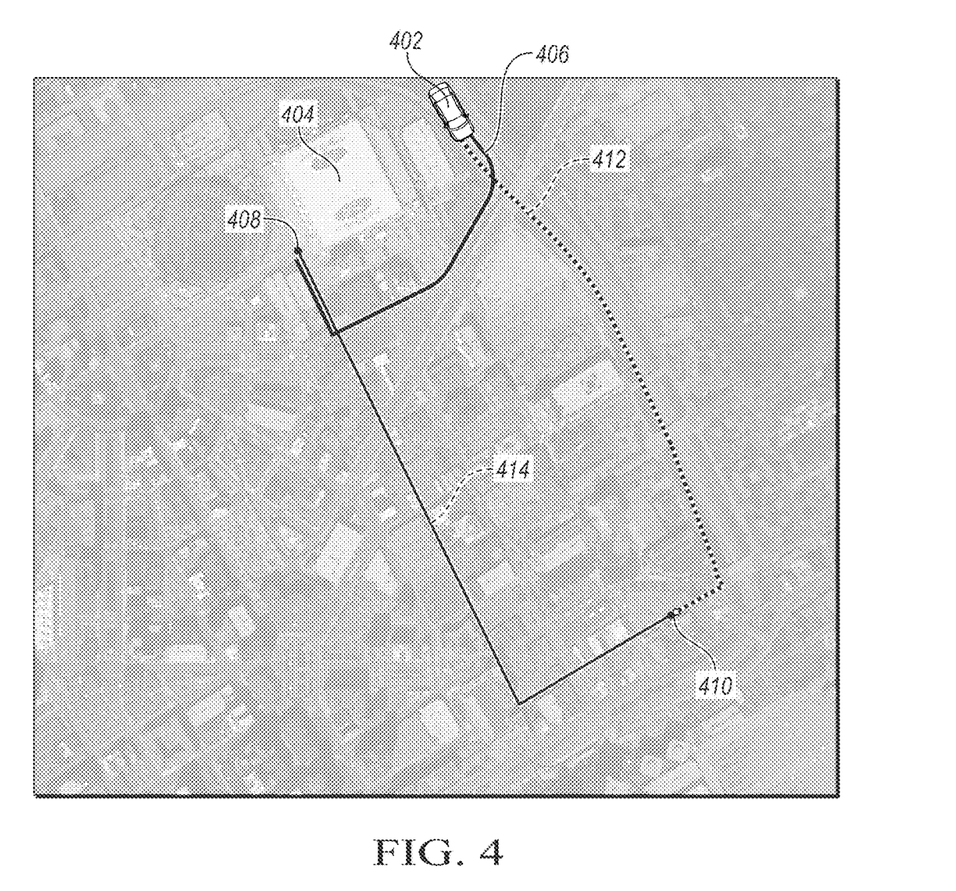
FIG. 4 is an exemplary geographic map illustrating vehicle routing alternatives based on fitness goals.

FIG. 4 is an exemplary geographic map illustrating vehicle routing alternatives based on fitness goals. A driver of a vehicle wearing an activity tracking device at a current location 402 with a final destination 404 may use a computing system, such as a navigation system including GPS, to route a path to the destination. The routing options may include shortest time, shortest distance, avoiding toll roads or avoiding highways. An exemplary shortest time route 406 may direct the user directly to the destination 404 having a street address 408. Based on fitness goals of the driver, the computing system may provide a recommended parking location 410. The recommended parking location 410 would route the driver to travel via vehicle along a recommended route 412 to arrive at the recommended parking location 410. The computing system would then provide a walking route 414 for the driver to walk. The destination 404 may be entered as a final destination or as an event destination. For example, if the destination 404 is entered as an event destination, the driver may enter a location and time the event begins. The vehicle computing system may then determine a recommended parking location 410 based on the current number of steps the driver has taken and an estimated number of steps required along the walking route 414. Because this is an event destination, the estimated number of steps required along the walking route 414 may be counted twice as the driver would walk to the event and then walk back to the vehicle from the event. Also, recommended parking location 410 may be based on time. For example as in the previous example, if an event destination was provided with an event starting time, the computing system may calculate the additional time required to drive along a recommended route 412 to the recommended parking location 410 and the time required to walk along the walking route 414 such that the recommended parking location would compensate so the recommended parking location would not result in the driver being late for the event.

Figure 5:
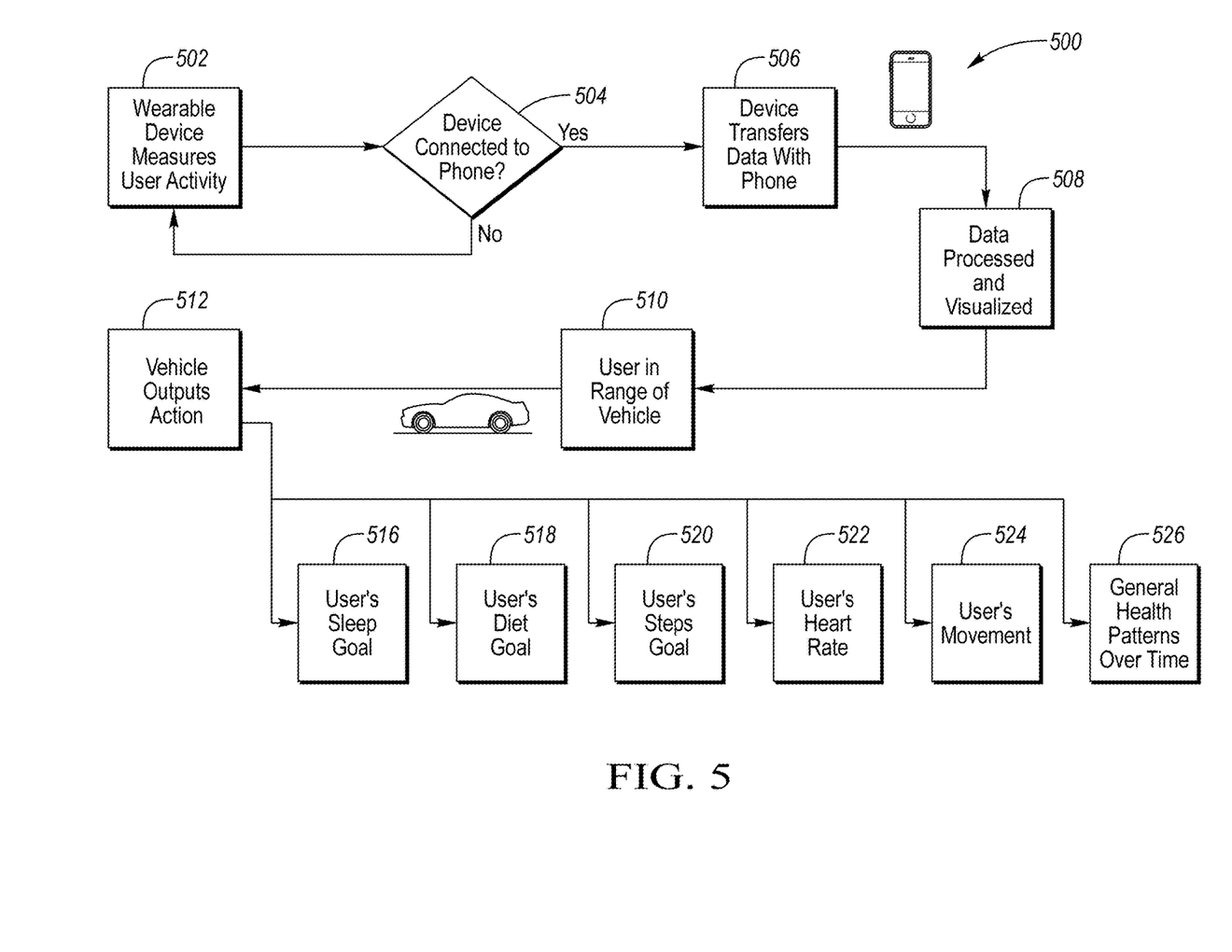
FIG. 5 is an exemplary flow diagram of interaction between an activity tracking device and a vehicle computing system.

FIG. 5 is an exemplary flow diagram 500 of interaction between an activity tracking device and a vehicle computing system. An individual wearing the activity tracking device has biometric characteristics detected and recorded 502. The activity tracking device may also scan wire and wireless connections to detect if a mobile phone is capable of being in communication with the activity tracking device. If the mobile phone connects and authenticates with the activity tracking device 504, data can be exchanged between the mobile phone and the activity tracking device 506. The mobile phone may either process the data or utilize an external computing system such as a cloud based system to process the data. The data after being processed may be displayed on the mobile phone display 508. This processed data may include biometric and non-biometric data, statistics and user goals. When a nomadic device (mobile phone or activity tracking device) is in range of a wire or wireless connection with the vehicle, the nomadic device may connect with the vehicle 510. Also, the nomadic device may continually connect with a remote system or server, such that the data from the nomadic device may be updated and available to the vehicle 510. When the user approaches the car, the vehicle may transfer data as to which user goals the user has and has not met within a predetermined time. The vehicle may then exchange data with the nomadic device. Based on the data from the nomadic device, the vehicle may recommend certain actions 512 based on goals currently not achieved. The goals may be sleep goal 516 (quality of sleep and duration), dietary goals 518, step goal 520, heart rate goal 522, movement 524, and general health patterns 526.

Figure 6:
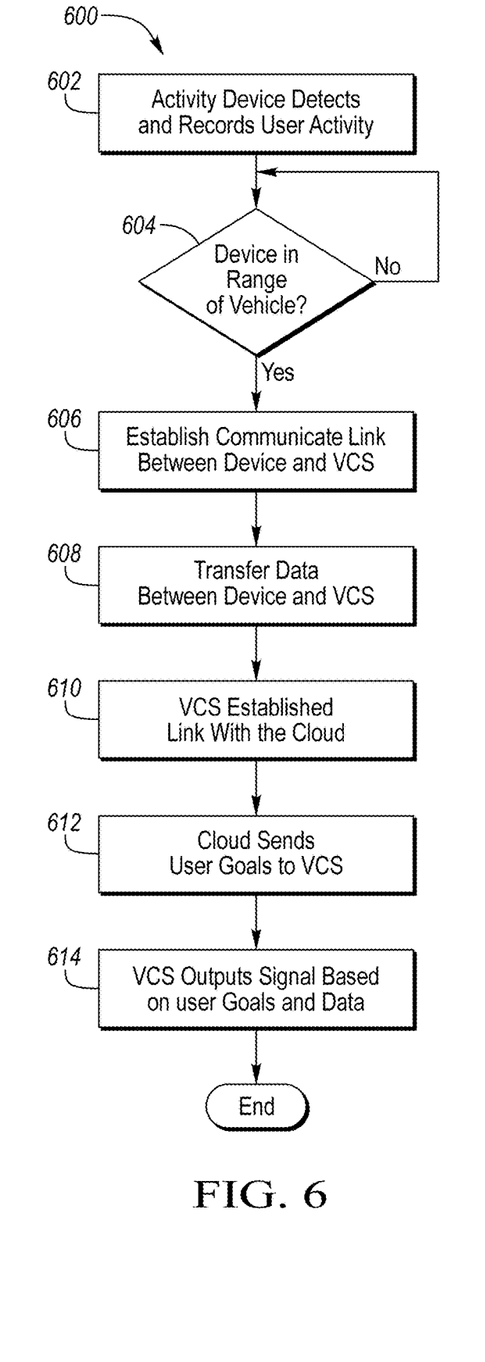
FIG. 6 is an exemplary flow diagram of interaction between an activity tracking device and a vehicle computing system.

FIG. 6 is an exemplary flow diagram 600 of interaction between an activity tracking device and a vehicle computing system. An activity tracking device detects and measures biometric characteristics at step 602 including movement, heart rate, skin temperature, $O_2$ saturation, skin conductivity, sweat or moisture. Based on the biometric characteristics, the activity tracking device alone or in conjunction with another processor may determine user aspects such as hours of sleep a user has had within a predetermined period and a sleep quality index of the sleep over a period of time. A connection between the activity tracking device and a vehicle is checked at step 604. When the activity tracking device is connected to the vehicle, a communication link is established at step 606. Data is transferred between the activity tracking device and VCS at step 608. The data may be biometric and non-biometric data. The VCS may establish connection with the cloud as shown at step 610. The cloud connection may allow the VCS to upload data to the cloud so that the data may be processed and the processed data and user goals stored in the cloud may be downloaded back to the VCS as shown at step 612. The VCS may output signals based on the goals and data as shown at step 614. The output signals may be used to drive a visual display, an audible alert, or may be sent to a vehicle module to control vehicle operation such as adaptive cruise control or LDW.

Figure 7:
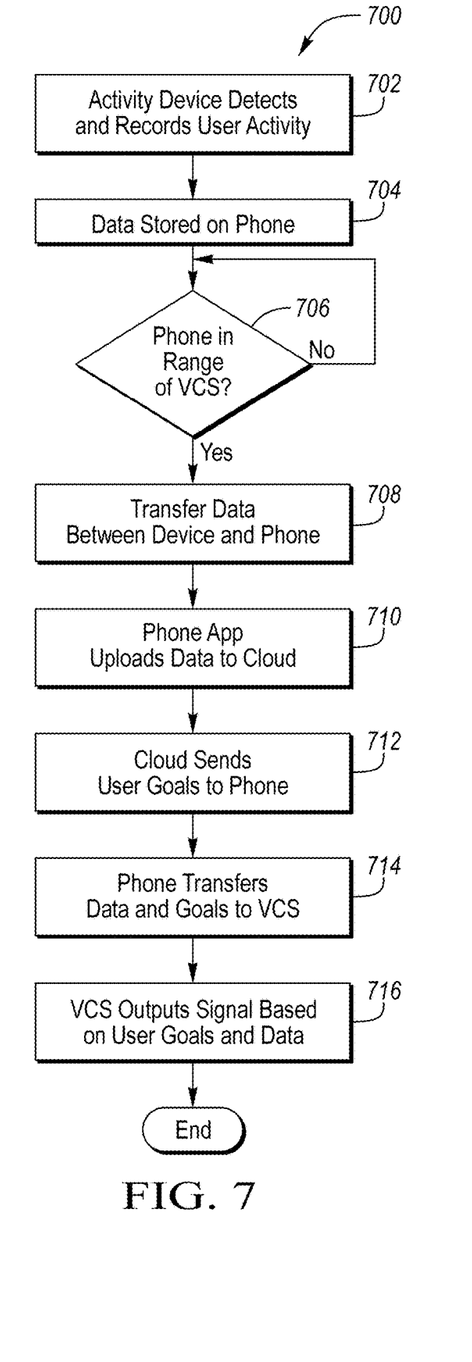
FIG. 7 is an exemplary flow diagram of interaction between an activity tracking device and a vehicle computing system via a mobile phone.

FIG. 7 is an exemplary flow diagram 700 of interaction between an activity tracking device and a vehicle computing system via a mobile phone. An activity tracking device detects and measures biometric characteristics at step 702 including movement, heart rate, skin temperature, $O_2$ saturation, skin conductivity, sweat or moisture. Based on the biometric characteristics, the activity tracking device alone or in conjunction with anther processor may determine user aspects such as hours of sleep a user has had within a predetermined period and a sleep quality index of the sleep over a period of time. A connection between the activity tracking device and a phone is made and data is shared at step 704. The vehicle scans for devices in range or connected via a wire. When a device is detected, the phone software initiates transfer of the most up-to-date information from the activity tracking device to the phone at step 708. The phone application then uploads data to an external server (e.g., the cloud) at step 710. The external server (e.g., the cloud) then processes the data and downloads processed data and the user goal at step 712. The phone transfers data, processed data and user goals at step 714 to the VCS. The VCS may output signals based on the goals and data as shown at step 716. The output signals may be used to drive a visual display, an audible alert, or may be sent to a vehicle module to control vehicle operation such as adaptive cruise control or LDW. In an alternative embodiment, after step 710, the VCS may then access the data directly from the cloud then progressing directly to step 716.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

What is claimed is:

1. A vehicle comprising:
   at least one processor programmed to
      generate an alert in response to a distance between the vehicle and a lane boundary the vehicle is traveling in falling below a threshold distance,
      communicate with a personal activity tracking device configured to detect a biometric characteristic of a driver of the vehicle, and
      increase the threshold distance based on the biometric characteristic.

2. The vehicle of claim 1, wherein the biometric characteristic is a number of hours the driver slept during a predetermined period of time.

3. The vehicle of claim 1, wherein the biometric characteristic includes a current heart rate and an average heart rate of the driver.

4. The vehicle of claim 1, wherein the biometric characteristic includes a comparison to a sleep quality index rating.

5. The vehicle of claim 1, wherein the at least one processor is programmed to communicate with the activity tracking device via a mobile phone.

6. The vehicle of claim 1, wherein the at least one processor is further programmed to increase the threshold distance based on an altitude of the vehicle.

* * * * *